US012745905B2

(12) United States Patent
Copland

(10) Patent No.: US 12,745,905 B2
(45) Date of Patent: Sep. 29, 2026

(54) METHODS AND SYSTEMS FOR DETERMINING CHANGE IN EYE POSITION BETWEEN SUCCESSIVE EYE MEASUREMENTS

(71) Applicant: AMO Development, LLC, Irvine, CA (US)

(72) Inventor: Richard J. Copland, Albuquerque, NM (US)

(73) Assignee: AMO Development, LLC, Irvine, CA (US)

( * ) Notice: Subject to any disclaimer, the term of this patent is extended or adjusted under 35 U.S.C. 154(b) by 334 days.

(21) Appl. No.: 18/642,651

(22) Filed: Apr. 22, 2024

(65) Prior Publication Data

US 2024/0268661 A1 Aug. 15, 2024

Related U.S. Application Data

(63) Continuation of application No. 17/229,789, filed on Apr. 13, 2021, now Pat. No. 11,963,722.

(51) Int. Cl.

| | |
|---|---|
| ***A61B 3/113*** | (2006.01) |
| ***A61B 3/00*** | (2006.01) |
| ***A61B 3/10*** | (2006.01) |

(52) U.S. Cl.

CPC ............ *A61B 3/113* (2013.01); *A61B 3/0025* (2013.01); *A61B 3/102* (2013.01)

(58) Field of Classification Search

CPC ....... A61B 3/113; A61B 3/0025; A61B 3/102; A61B 3/14

See application file for complete search history.

(56) References Cited

U.S. PATENT DOCUMENTS

| | | | |
|---|---|---|---|
| 5,347,327 | A | 9/1994 | Sekine et al. |
| 5,777,719 | A | 7/1998 | Williams et al. |

(Continued)

FOREIGN PATENT DOCUMENTS

| | | |
|---|---|---|
| EP | 3127472 A1 | 2/2017 |
| EP | 3222204 A1 | 9/2017 |

(Continued)

OTHER PUBLICATIONS

Chong C., et al., "Large Coherence Length Swept Source for Axial Length Measurement of the Eye," Applied Optics, Apr. 2009, vol. 48 (10), pp. D144-D150.

(Continued)

*Primary Examiner* — Tuyen Tra

(57) ABSTRACT

A measurement instrument and method: produce light having a linear shape; direct the light toward an eye and provide returned light, having the linear shape, from the eye to a split-prism; split the returned light into first and second linear segments and image them onto an image sensor; determine a first lateral offset between the first and second linear segments on the image sensor at a first time; determine a second lateral offset between them at a second time; determine a difference between the first and second lateral offsets; determine a distance that the eye moved relative to the first lens between the first time and the second time based on the difference between the first and second lateral offsets; perform optical coherence tomographer (OCT) measurements at the first and second times; and combine the OCT measurements while compensating for eye movement based on the determined eye movement.

16 Claims, 10 Drawing Sheets

(56) References Cited

U.S. PATENT DOCUMENTS

| | | | | |
|---|---|---|---|---|
| 6,550,917 | B1 | 4/2003 | Neal et al. | |
| 6,922,250 | B2 | 7/2005 | Fercher | |
| 7,370,966 | B2 | 5/2008 | Fukuma et al. | |
| 7,480,059 | B2 | 1/2009 | Zhou et al. | |
| 7,800,759 | B2 | 9/2010 | Lai et al. | |
| 7,980,699 | B2 | 7/2011 | Neal et al. | |
| 8,016,418 | B2 | 9/2011 | Kawai et al. | |
| 8,199,329 | B2 | 6/2012 | Blalock et al. | |
| 9,259,148 | B2 | 2/2016 | Bajramovic et al. | |
| 9,364,144 | B2 | 6/2016 | Hacker et al. | |
| 9,554,700 | B2 * | 1/2017 | Nakahara | A61B 3/102 |
| 9,717,408 | B2 | 8/2017 | Akiba et al. | |
| 11,782,279 | B2 | 10/2023 | Ouderkirk et al. | |
| 2007/0268456 | A1 | 11/2007 | Ohbayshi et al. | |
| 2014/0098345 | A1 | 4/2014 | Cai et al. | |
| 2015/0116662 | A1 | 4/2015 | Wada | |
| 2021/0267799 | A1 | 9/2021 | Neal et al. | |

FOREIGN PATENT DOCUMENTS

| | | | |
|---|---|---|---|
| JP | H04322634 | A | 11/1992 |
| JP | 2017006456 | A | 1/2017 |

OTHER PUBLICATIONS

Grajciar B., et al., "High Sensitive Measurement of the Human Axial Eye Length in Vivo With Fourier Domain Low Coherence Interferometry," Optics Express, Feb. 2008, vol. 16 (4), pp. 2405-2414.

Mejia-Barbosa Y., et al., "Object Surface For Applying A Modified Hartmann Test To Measure Corneal Topography," Applied Optics, Nov. 1, 2001, vol. 40 (31), pp. 5778-5786.

Ruggeri M., et al., "Imaging and Full-length Biometry of the Eye During Accommodation Using Spectral Domain OCT With an Optical Switch," Biomedical Optics Express, Jun. 2012, vol. 3 (7), pp. 1506-1520.

* cited by examiner

101

4000

METHODS AND SYSTEMS FOR DETERMINING CHANGE IN EYE POSITION BETWEEN SUCCESSIVE EYE MEASUREMENTS

CROSS REFERENCE TO RELATED APPLICATIONS

This application claims priority to and is a continuation of U.S. patent application Ser. No. 17/229,789, filed Apr. 13, 2021, which is incorporated herein by reference in its entirety.

TECHNICAL FIELD

Embodiments of this invention pertain to eye measurement systems and methods, and more particularly, to eye measurement systems and methods which can determine a change in an eye's position between a first eye measurement at a first time and a subsequent second eye measurement at a second time, for example due to eye movement.

BACKGROUND

Various types of eye measurement instruments and methods are known, including autorefractors, wavefront aberrometers, corneal topographers and optical coherence topography (OCT) systems.

An autorefractor is a computer-controlled machine used during an eye examination to provide an objective measurement of the refractive error for an eye which can be used to generate a prescription for glasses or contact lenses. This is achieved by measuring how light is changed as it enters a person's eye.

Wavefront aberrometry measures the way a wavefront of light passes through the cornea and the crystalline lens of an eye, which are the refractive components of the eye. Distortions that occur as light travels through the eye are called aberrations, representing specific vision errors. Various types of wavefront aberrometers and methods are known, including Tscherning aberrometers, retinal ray tracing, and Shack-Hartmann aberrometers.

Corneal topography, also sometimes referred to as photokeratoscopy and videokeratoscopy, is a technique that is used to map the curved surface of the cornea. Corneal topography data can help measure the quality of vision as well as assist in eye surgery and the fitting of contact lenses. Various types of corneal topographers and methods are known, including Placido ring topographers, Scheimpflug imagers, and more recently, point source color LED topographers (CLT).

Optical coherence tomography (OCT) is a method of interferometry that determines the scattering profile of a sample along the OCT beam. OCT systems can operate in the time domain (TD-OCT) or the frequency domain (FD-OCT). FD-OCT techniques have significant advantages in speed and signal-to-noise ratio as compared to TD-OCT. The spectral information discrimination in FD-OCT is typically accomplished by using a dispersive spectrometer in the detection arm in the case of spectral domain OCT (SD-OCT) or rapidly scanning a swept laser source in the case of swept-source OCT (SS-OCT).

FIG. 1 is a schematic drawing of a portion of a human eye 101 which can be used in the explanations below. Eye 101 includes, in relevant part, a cornea 402, an iris 404, a lens 406, a sclera 408 and a retina 409.

Knowledge of the structure of eye 101 is necessary to plan refractive and cataract surgeries for optimal outcomes. Some parameters of interest may include: anterior corneal radius, corneal thickness, posterior corneal radius, anterior chamber depth, anterior lens radius, lens thickness, posterior lens radius and total eye length. Many of these parameters can be measured with an OCT system, as described above.

OCT systems inherently have a usable measurement range known as the coherence length. Low-cost OCT systems, such as spectral-domain OCT (SD-OCT) systems, typically have coherence lengths of 8 mm or less. However a normal eye length is 25 mm, so an 8 mm length is insufficient to measure the entire length of eye 101 in a single scan.

Furthermore, eye movement of a patient or subject during measurements makes these short coherence lengths problematic. For instance, one could make a first OCT scan of a first portion of the eye, adjust the reference length of the OCT system, then make a second OCT scan of a second portion of the eye, and then combine the results of the first and second scans. However, poor results are obtained if the time between scans is more than about 30 milliseconds, due to eye movement of the patient or subject.

One solution to this problem is to use a swept-source system OCT (SS-OCT) system that inherently has a longer coherence length. However, SS-OCT systems tend to be expensive.

Another solution is to use a fast optical means to switch between different length reference legs in the SD-OCT system and then combine the two OCT scans. Fiber optic switches are often used for this fast switching, but electro-optic mirrors may be used instead. Regardless, this is again a relatively expensive solution. On the other hand, if less expensive mechanical movement mechanisms are employed for the switching, then the time required between successive measurements is typically on the order of 200 milliseconds, which is significantly greater than the 30 millisecond limit mentioned above for obtaining acceptable results.

Yet another solution uses a time domain OCT (TD-OCT) system. However, TD-OCT systems can't be combined with scan mirrors to provide additional shape information of structures on an eye such as corneal curvature, thickness maps or anterior chamber dimensions. So, in general, TD-OCT systems are much less desirable than SD-OCT and SS-OCT systems.

Thus it is desired to provide a less expensive measurement instrument and method which can combine data from successive eye measurements (e.g., OCT measurements; corneal topography measurements) even in the presence of significant eye movement between the successive measurements.

SUMMARY OF THE INVENTION

In one aspect, an instrument comprises: a light source configured to produce light having a linear shape; a beamsplitter configured to receive the light from the light source and to direct the light in a first direction; a first lens located one focal length from the light source and configured to receive the light from the beamsplitter and direct the light to an eye to produce a virtual image of the linear shape in the eye, and further configured to receive returned light from the eye and provide the returned light to the beamsplitter, wherein the beamsplitter is further configured to direct the returned light in a second direction; and a split-prism rangefinder including an image sensor, wherein the split-prism rangefinder is configured to receive the returned light from the beamsplitter and to determine a distance the eye moved relative to the first lens between a first time and a second time which is subsequent to the first time, based on a change in the linear shape of the returned light which is imaged onto the image sensor.

In some embodiments, the split-prism rangefinder further comprises: a second lens; a split-prism; and a third lens. The second lens is configured to receive the returned light from the beamsplitter and provide the returned light to the split-prism, the split-prism is configured to receive the returned light from the second lens and provide the returned light to the third lens; and the third lens is configured to image the returned light onto the image sensor.

In some embodiments, the split-prism is configured to split the returned light into a first linear segment and a second linear segment, wherein the first linear segment and the second linear segment are both imaged onto the image sensor.

In some embodiments, the image sensor comprises one of a complementary metal oxide semiconductor (CMOS) sensor and a line scan sensor, and includes a plurality of pixels onto which the returned light including the first linear segment and the second linear segment is imaged.

In some embodiments, the instrument further comprises a processor configured to receive an image signal from the image sensor, wherein the image signal is generated from outputs of the pixels in response to the returned light including the first linear segment and the second linear segment.

In some embodiments, the processor is configured process the image signal to determine a first lateral offset between the first linear segment and the second linear segment at the first time, and to determine a second lateral offset between the first linear segment and the second linear segment at the second time, and to determine the distance the eye has moved relative to the first lens between the first time and the second time based on a difference between the first lateral offset and the second lateral offset.

In some embodiments, the processor is configured to determine the first lateral offset between the first linear segment and the second linear segment at the first time by determining a fractional number of pixels between a center line of the imaged first linear segment and a center line of the imaged second linear segment on the image sensor at the first time.

In another aspect, a method comprises: producing light having a linear shape; direct the light toward an eye via a first lens located one focal length from the light source to produce a virtual image of the linear shape in the eye; receiving returned light from the eye and providing the returned light to a split-prism; splitting the returned light into a first linear segment and a second linear segment, by the split-prism; imaging the first linear segment and the second linear segment onto an image sensor; determining a first lateral offset between the first linear segment and the second linear segment on the image sensor at a first time; determining a second lateral offset between the first linear segment and the second linear segment on the image sensor at a second time which is subsequent to the first time; determining a difference between the first lateral offset and the second lateral offset; and determining a distance that the eye moved relative to the first lens between the first time and the second time based on the difference between the first lateral offset and the second lateral offset.

In some embodiments, the image sensor includes a plurality of pixels onto which the returned light including the first linear segment and the second linear segment is imaged, wherein the method further comprises the image sensor providing an image signal to a processor, wherein the image signal is generated from outputs of the pixels in response to the returned light including the first linear segment and the second linear segment.

In some embodiments, the method further comprises the processor processing the image signal to determine the first lateral offset between the first linear segment and the second linear segment at the first time, to determine the second lateral offset between the first linear segment and the second linear segment at the second time, to determine the difference between the first lateral offset and the second lateral offset, and to determine the distance the eye has moved relative to the first lens between the first time and the second time based on the difference between the first lateral offset and the second lateral offset.

In some embodiments, the method further comprises: determining a fractional number of pixels between a center line of the imaged first linear segment and a center line of the imaged second linear segment on the image sensor at the first time; and determining the first lateral offset between the first linear segment and the second linear segment from the fractional number of pixels between the center line of the imaged first linear segment and the center line of the imaged second linear segment on the image sensor.

In some embodiments, the method further comprises: measuring a first portion of a distance within the eye at the first time; measuring a second portion of the distance within the eye at the second time; and determining the distance within the eye from the measured first portion, the measured second portion, and the determined distance that the eye has moved relative to the first lens between the first time and the second time.

In some embodiments, the first portion and the second portion are measured by optical coherence tomography.

In yet another aspect, an instrument comprises: a light source configured to produce light having a linear shape; an optical coherence tomographer (OCT) configured to output an eye measurement laser beam; a first beamsplitter configured to receive the light from the light source and to direct the light in a first direction; a second beamsplitter configured to receive the eye measurement laser beam and the light from first beamsplitter; a first lens located one focal length from the light source and configured to receive the light and the eye measurement laser beam from the second beamsplitter, to direct the light to an eye to produce a virtual image of the linear shape in the eye, and to direct the eye measurement laser beam to the eye, and further configured to receive returned light from the eye and a return eye measurement laser beam from the eye and to provide the returned light and the return eye measurement laser beam to the second beamsplitter, wherein the second beamsplitter is further configured to direct the returned light to the first beamsplitter and to direct the return eye measurement laser beam to the OCT; a second lens; a split-prism; a third lens; an image sensor; and a processor. The second lens is configured to receive the returned light from the first beamsplitter and provide the returned light to the split-prism, the split-prism is configured to receive the returned light from the second lens and provide the returned light to the third lens; the third lens is configured to image the returned light onto the image sensor, the image sensor is configured to output an image signal to the processor, the processor is configured to process the image signal to determine a change in the linear shape of the returned light on the image sensor from a first time to a second time subsequent to the first time, and to determine a distance the eye moved relative to the first lens between the first time and the second time based on the change in the linear shape of the returned light which is imaged onto the image sensor, the OCT is configured to measure a first portion of a distance within the eye at the first time using the return eye measurement laser beam; the OCT is configured to measure a second portion of the distance within the eye at the second time using return eye measurement laser beam; and the processor is configured to determine the distance within the eye from the measured first portion, the measured second portion, and the determined distance that the eye moved relative to the first lens between the first time and the second time.

In some embodiments, the split-prism is configured to split the returned light into a first linear segment and a second linear segment, wherein the first linear segment and the second linear segment are both imaged onto the image sensor In some embodiments, the image sensor comprises includes a plurality of pixels onto which the returned light including the first linear segment and the second linear segment is imaged, and wherein the image signal is generated from outputs of the pixels in response to the returned light including the first linear segment and the second linear segment.

In some embodiments, the processor is configured process the image signal to determine a first lateral offset between the first linear segment and the second linear segment at the first time, and to determine a second lateral offset between the first linear segment and the second linear segment at the second time, and to determine the distance the eye has moved relative to the first lens between the first time and the second time based on a difference between the first lateral offset and the second lateral offset.

In some embodiments, the processor is configured to determine the first lateral offset between the first linear segment and the second linear segment at the first time by determining a fractional number of pixels between a center line of the imaged first linear segment and a center line of the imaged second linear segment on the image sensor at the first time.

In some embodiments, the processor is configured to determine the distance the eye has moved relative to the first lens between the first time and the second time further based on a prism angle of the split-prism, an index of refraction of the split-prism, a magnification of the third lens, a pixel size of the image sensor.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation. As used herein, "approximately" means with 30% (i.e., +/−30%) of a nominal value.

As used herein a linear shape refers to the shape of a real line having a length and an actual width, rather than a theoretical line which has no length. Accordingly, the linear shape may be considered as the shape of a rectangle where the length is much greater than the width such that it appears to be a line. Similarly, a linear segment refers to a line segment of a real line having a length and an actual width, rather than a theoretical line which has no length. Accordingly, the linear segment may be considered to have the shape of a rectangle where the length is much greater than the width such that it appears to be a line. Furthermore, as the linear segment has an actual width, there is a centerline which extends down the length and is centered within the width of the linear segment.

Figure 1:
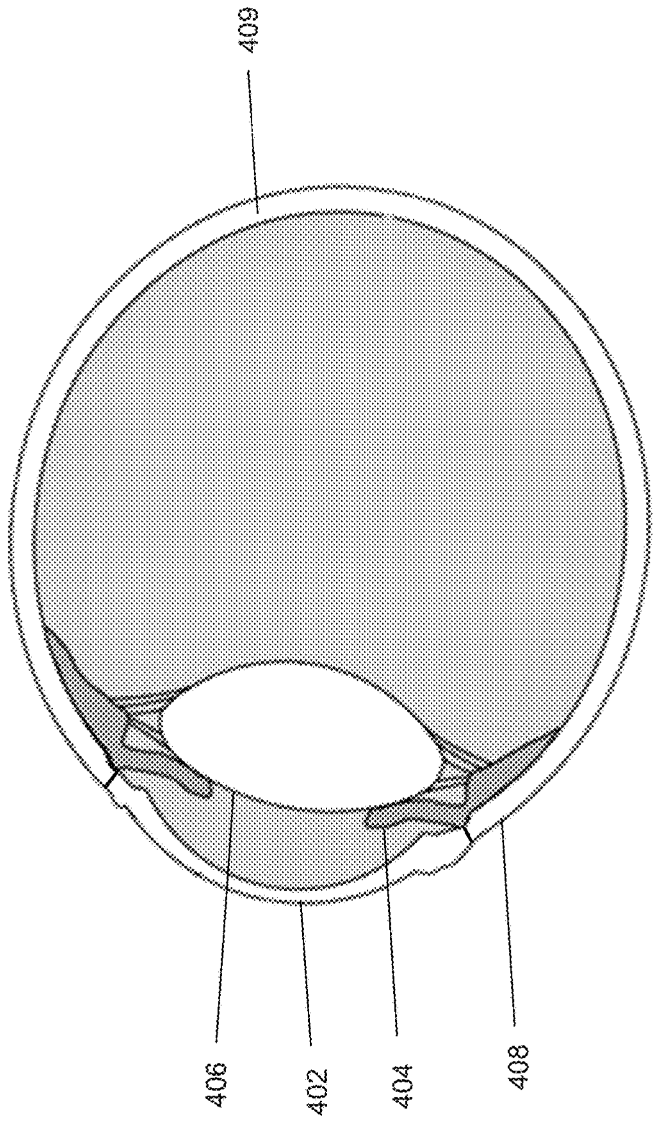
FIG. 1 (Prior Art)
FIG. 1 is a schematic drawing of a portion of a human eye.
Figure 2A:
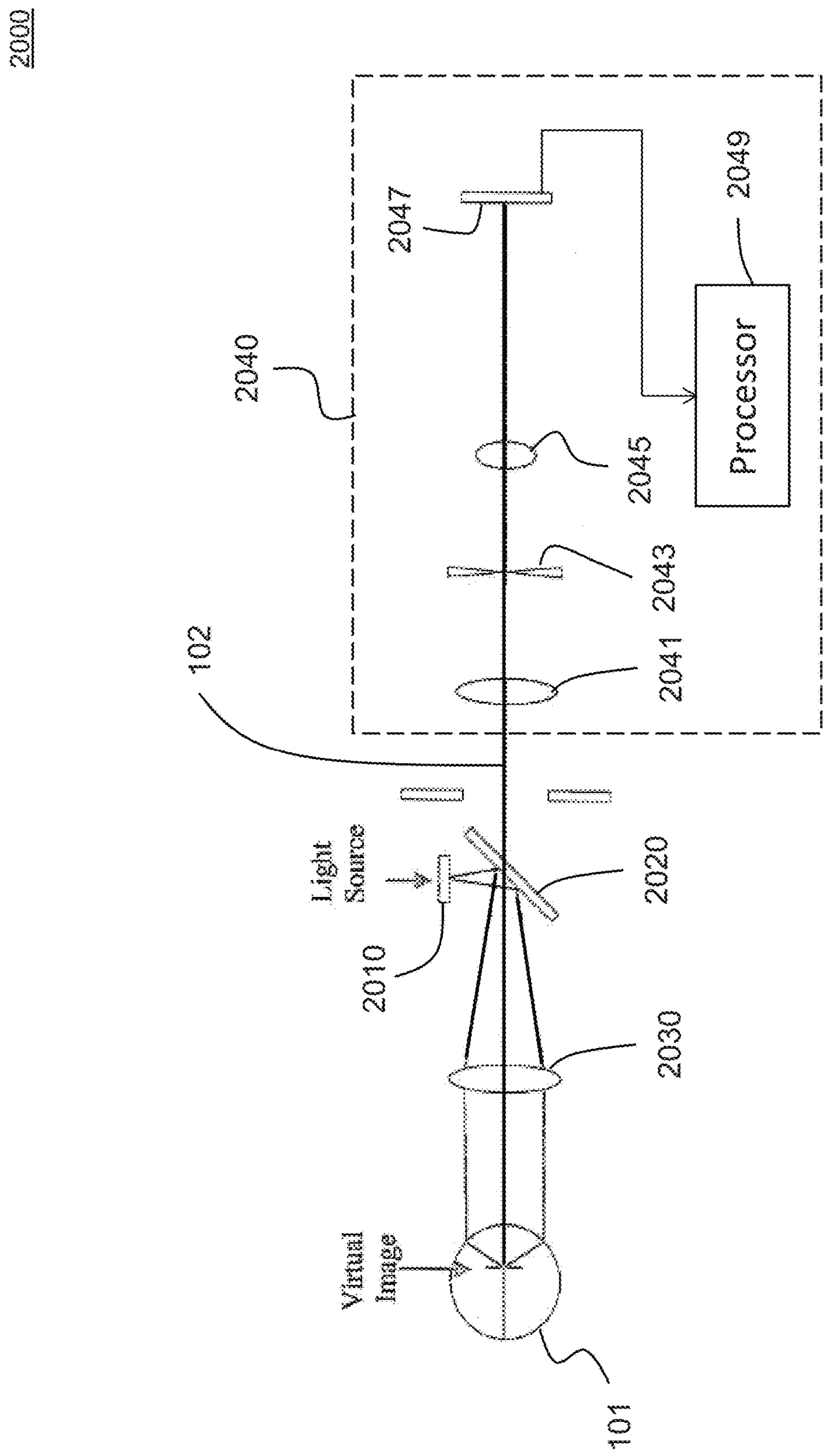
FIG. 2A illustrates supplying light to an eye with an embodiment of an instrument which includes a split-prism rangefinder.

FIG. 2A illustrates supplying light to an eye with an embodiment of an instrument 2000 which includes a split-prism rangefinder. Instrument 2000 includes a reference or range-finding light source 2010, a beamsplitter 2020, a first lens 2030 and a split-prism rangefinder 2040. Split-prism rangefinder 2040 includes a second lens 2041, a split-prism 2043, a third lens 2045, an image sensor 2047, and a processor 2049. Beneficially, first lens 2030 is disposed one focal length away from reference light source 2010.

In some embodiments, processor 2049 may not be a dedicated part of split-prism rangefinder 2040, but instead may be a shared processor of instrument 2000 which may include other components such an OCT system, a corneal topographer, a wavefront aberrometer, etc. as discussed below. In that case, processor 2049 may include execute instructions stored in a memory device to perform one or more algorithms for determining the distance that eye 101 moves between a first time and a second time subsequent to the first time, as described below.

In operation, light from reference light source 2010 reflects off beam splitter 2020. Reference or range finding light rays from reference light source 2010 are collimated leaving first lens 2030. A virtual image of reference light source 2010 is created behind the cornea of eye 101. Because the light rays are collimated, the location of the virtual image relative to the apex of the cornea is the same for any distance of eye 101. A convenient shape for the reference or range-finding light is a vertical line.

Figure 2B:
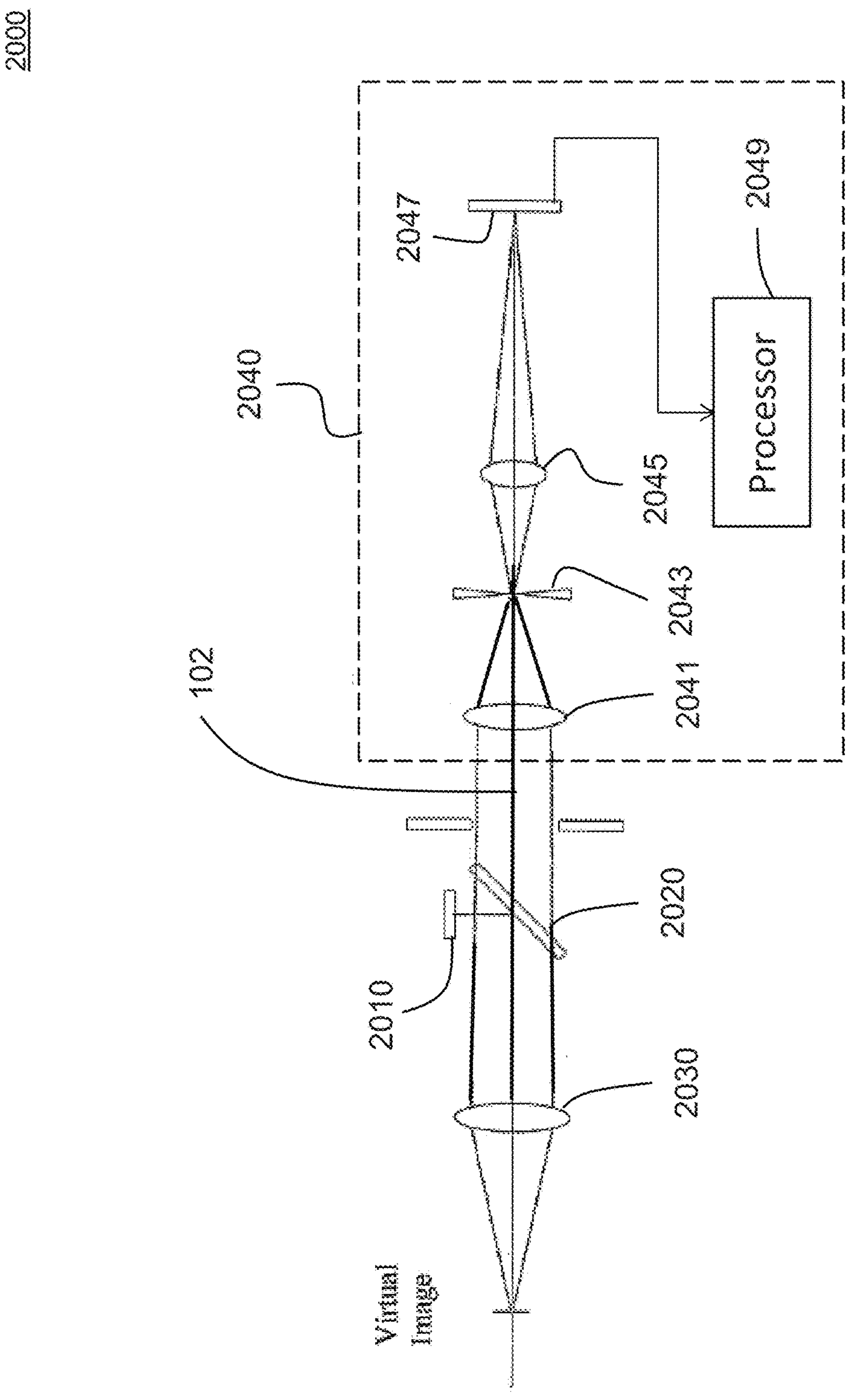
FIG. 2B illustrates imaging returned light from an eye with an embodiment of an instrument which includes a split-prism rangefinder.
Figure 3C:
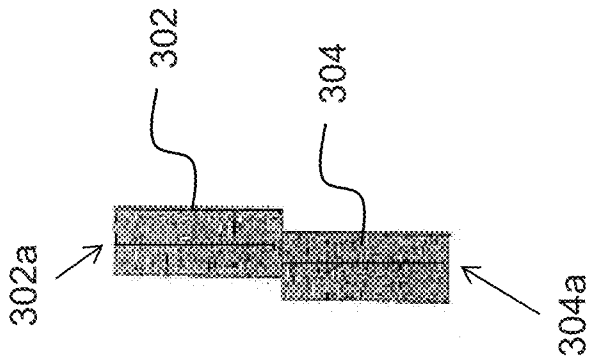
FIGS. 3A, 3B and 3C illustrate examples of linear segments of imaged light appearing on an image sensor from a split-prism.
Figure 3B:
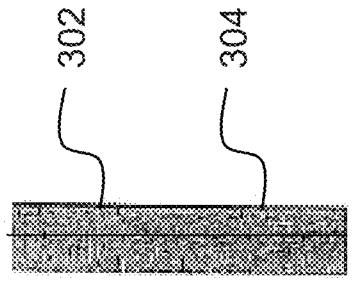
Figure 3A:
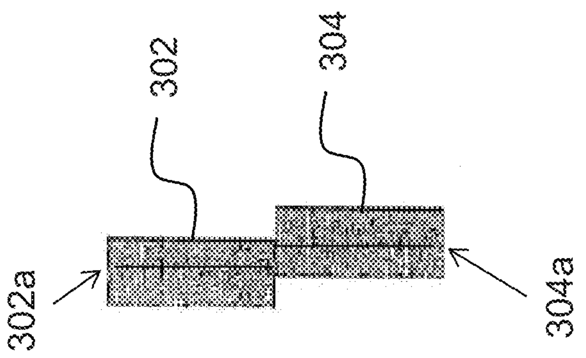

FIG. 2B illustrates imaging returned light from eye 101 with instrument 2000. The returned light from eye 101 is used to image the linear shape onto image sensor 2047, which may be a simple CMOS camera sensor that is used as a rangefinder sensor. When the virtual image is located at a position that focuses on split-prism 2043, the rangefinder image sensor 2047 sees a single straight linear shape. However, when the image is displaced along the optical axis 102, the linear shape changes. In particular, the linear shape splits into a first linear segment 302 and a second linear segment 304, as shown in FIGS. 3A, 3B and 3C. The amount of splitting, or displacement of the first and second linear segments, is proportional to the displacement of the image from being focused at split-prism 2043 due to displacement of eye 101. So distances, including the displacement or movement of eye 101, may be calculated.

FIGS. 3A, 3B and 3C illustrate examples of linear segments of imaged light appearing on image sensor 2047 from split-prism 2043. In particular: FIG. 3A illustrates the image on range finder sensor 2047 when the virtual image focuses in front of split-prism 2043; FIG. 3B illustrates the image on range finder sensor 2047 when the virtual image focuses on split-prism 2043; and FIG. 3C illustrates the image on range finder sensor 2047 when the virtual image focuses behind split-prism 2043. The relationships between first linear segment 302, having a first centerline 302*a*, and second linear segment 304, having a second centerline 304*a*, is shown for each of these situations. In particular, it is seen that in FIGS. 3A and 3C there is a lateral offset between first centerline 302*a* and second centerline 304*a* which depends on how far the virtual image is formed from split-prism 2043, which in turn depends on the relative location of eye 101 with respect to instrument 2000, including reference light source 2010. Accordingly, the movement of eye 101 between a first time and a second time may be determined by a change in the lateral offset between first centerline 302*a* and second centerline 304*a* from the first time to the second time.

In operation, reference light source 2010 is configured to produce light having a linear shape. Beamsplitter 2020 is configured to receive the light from reference light source 2010 and direct the light in a first direction (i.e., toward eye 101). First lens 2030 is located one focal length from reference light source 2010 and is configured to receive the light from beamsplitter 2020 and direct the light to eye 101 to produce a virtual image of the linear shape in the eye, and is further configured to receive returned light from eye 101 and provide the returned light to beamsplitter 2020. Beamsplitter 2020 is further configured to direct the returned light in a second direction (i.e., toward split-beam rangefinder 2040). Split-prism rangefinder 2040 is configured to receive the returned light from beamsplitter 2020 and to determine a distance that eye 101 moved relative to first lens 2030 between a first time and a second time which is subsequent to the first time, based on a change in the linear shape of the returned light which is imaged onto image sensor 2047.

Split-prism 2043 is configured to split the returned light into a first linear segment 302 and a second linear segment 304, wherein the first linear segment and the second linear segment are both imaged onto image sensor 2047.

Beneficially, image sensor 2047 comprises a complementary metal oxide semiconductor (CMOS) sensor or a line scan sensor, and includes a plurality of pixels onto which the returned light including first linear segment 302 and second linear segment 304 is imaged.

Processor 2049 is configured to receive an image signal from image sensor 2047, wherein the image signal is generated from outputs of the pixels in response to the returned light including the first linear segment 302 and the second linear segment 304.

Processor 2049 is configured process the image signal to determine a first lateral offset between first linear segment 302 and second linear segment 304 at the first time, and to determine a second lateral offset between first linear segment 302 and second linear segment 304 at the second time, and to determine the distance that eye 101 has moved relative to first lens 2030 between the first time and the second time based on a difference between the first lateral offset and the second lateral offset.

Processor 2049 is configured to determine the first lateral offset between first linear segment 302 and second linear segment 304 at the first time by determining a fractional number of pixels of image sensor 2047 between a first center line of the imaged first linear segment 302 and a second center line of the imaged second linear segment 304 on image sensor 2047 at the first time. Similarly, processor 2049 is configured to determine the second lateral offset between first linear segment 302 and the second linear segment 304 at the second time by determining a fractional number of pixels of image sensor 2047 between the first center line of the imaged first linear segment 302 and the second center line of the imaged second linear segment 304 on image sensor 2047 at the first time.

Beneficially, the split-prism rangefinder should be able to resolve distances similar to the axial length accuracy needed to implant an intraocular lens in an eye, which is about 0.01 mm.

The resolution achievable by instrument 2000 including the split-prism rangefinder may be calculated by considering that the ray through the center of third lens 2045 is undeviated, and the equation for the deviation through a thin prism is $D=(n-1)*A$, where D is the deviation, n is the index of refraction of the split-prism, and A is the apical angle of the prism.

For a practical example system, we assume unity magnification by first and second lenses 2030 and 2041. Then we suppose that during a first measurement (e.g., a first OCT scan) at a first time, the image may be focused at split-prism 2043. Then before the second measurement (e.g., a second OCT scan) at a subsequent second time, we suppose that eye 101 moves one millimeter. Assuming a 2-degree prism with an index of refraction, n, of 1.5, light rays exiting split-prism 2043 diverge from each other by 2 degrees, which is 0.035 milliradians. After traveling one millimeter the rays are split by 0.035 millimeters. Next we assume a magnification of ten to rangefinder sensor 2047, which is easily achieved with a simple third lens 2045. If we assume a pixel size of 0.0035 mm which is common for a modern camera sensor, movement of eye 101 by one millimeter corresponds to ten pixels on image sensor 2047, where one pixel corresponds to a size of 0.1 mm. With a long linear shape the centerline may be determined or resolved twenty times smaller than a pixel. So the assumed system would have a resolution of 0.005 mm which is two times better than the requirement expressed above. For the example described, a typical width of image sensor 2047 is 8 mm. So an optical magnification of ten means the width sampled on eye 101 would be 0.8 mm.

Figure 4:
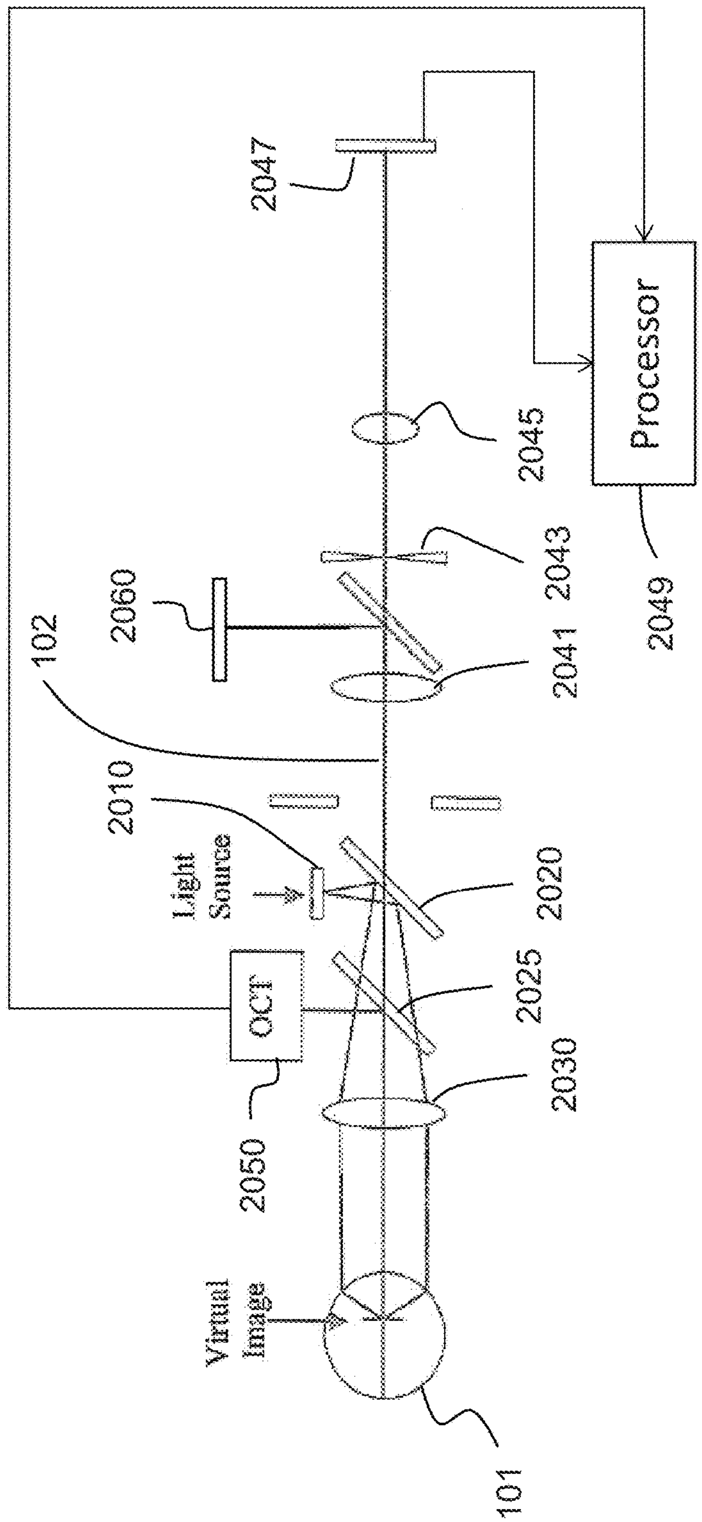
FIG. 4 illustrates supplying light and an eye measurement laser beam to an eye with an embodiment of an instrument which includes a split-prism rangefinder.

For a practical system an alignment camera with a wider field of view would allow an operator to align instrument 2000 to eye 101. The rangefinder light source 2010 would also be visible on the alignment camera. A suitable location for such an alignment camera 2060 is shown in FIG. 4, along with the incorporation of an OCT system 2050 which provided an OCT measurement laser beam to eye 101. FIG. 4 illustrates supplying light and an eye measurement laser beam to eye 101 with an embodiment of an instrument 4000 which includes a split-prism rangefinder, as discussed and described above with respect to FIGS. 2A, 2B and 3. Instrument 4000 includes a second beamsplitter 2025 for coupling both the light from reference light source 2010 and the eye measurement laser beam to eye 101 via first lens 2030.

It is also relevant to note that modern cameras costing less than a few hundred dollars may have frame rates of over 100 frames per second. So the images from image sensor 2047 can be read on timescales where eye motion is effectively frozen.

Figure 5:
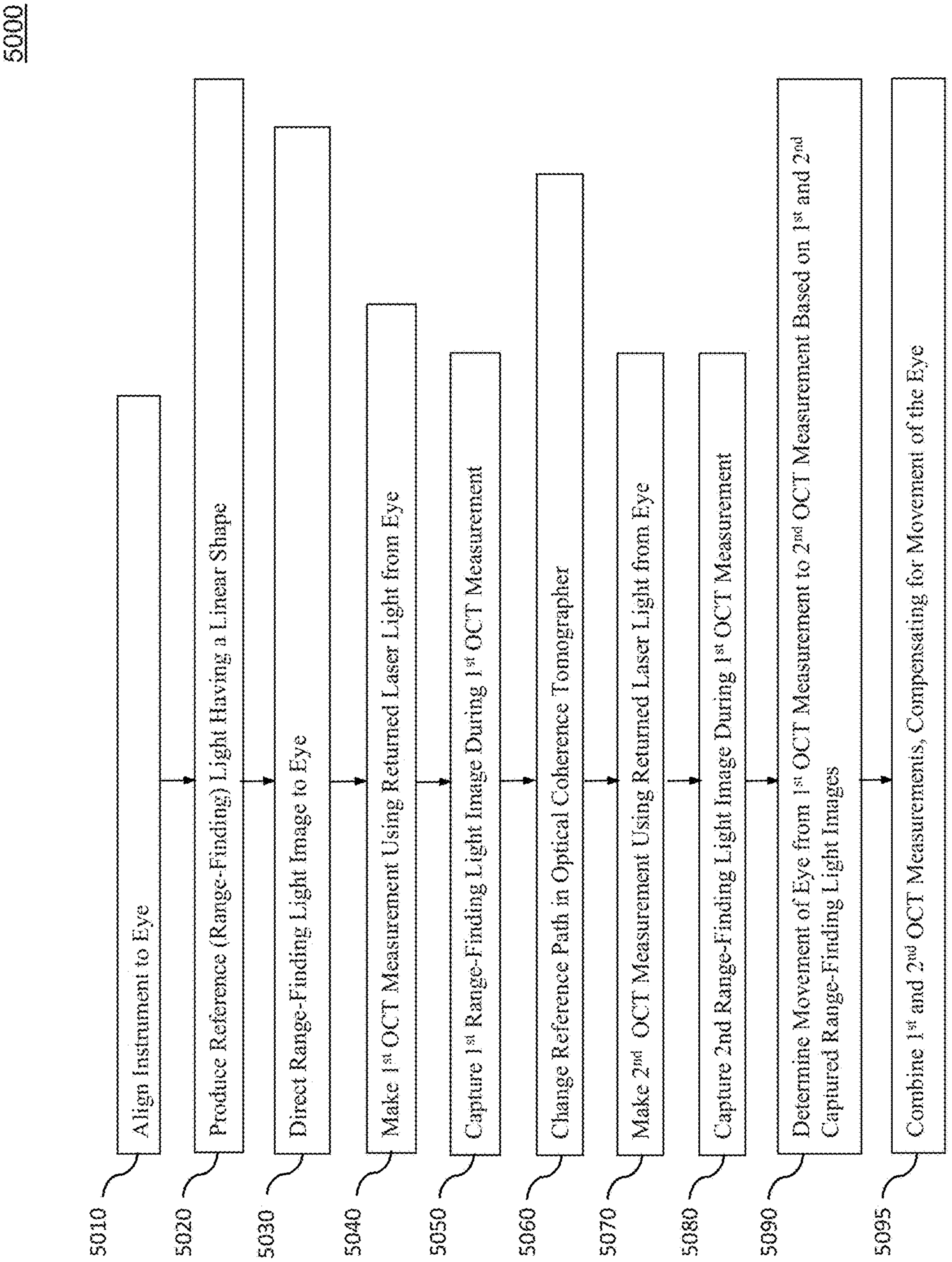
FIG. 5 is a flowchart of an example embodiment of a method of measuring an optical characteristic of an eye.

FIG. 5 is a flowchart of an example embodiment of a method 5000 of measuring one or more characteristics of an eye with an eye measurement instrument. An operation 5010 includes aligning the eye measurement instrument to the eye under examination. An operation 5020 includes producing reference (range-finding) light having a linear shape. An operation 5030 includes directing the reference or range-finding light toward an eye via an optical system. An operation 5040 includes making a first OCT measurement using returned OCT laser light from the eye at a first time. An operation 5050 includes capturing a first range-finding light image during the first OCT measurement. An operation 5060 includes changing the reference path in the OCT device. An operation 5070 includes making a second OCT measurement using returned OCT laser light from the eye at a second time. An operation 5080 includes capturing a second range-finding light image during the second OCT measurement. An operation 5090 includes determining a movement of the eye from the first OCT measurement (first time) to the second OCT measurement (second time) based on the first and second captured range-finding light images. An operation 5095 includes combining the first and second OCT measurements, compensating for movement of the eye that is determined in operation 5090. The first and second OCT measurements are respectively of a first and a second portion of the eye, as described earlier in this disclosure. This method solves the problem described earlier, i.e., the eye movement during OCT measurements may make short coherence lengths problematic; for instance, when combining the results of two successive OCT scans, poor results may be obtained due to eye movement of the patient or subject.

A method of operating the split-prism rangefinder 2040 may include the following operations. An operation includes aligning the eye measurement instrument to the eye under examination.

A further operation includes producing reference or range-finding light having a linear shape.

A further operation includes directing the reference or range-finding light toward an eye via a first lens located one focal length from the light source to produce a virtual image of the linear shape in the eye.

A further operation includes receiving returned light from the eye and providing the returned light to a split-prism.

A further operation includes the split-prism splitting the returned light into a first linear segment and a second linear segment.

A further operation includes imaging the first linear segment and the second linear segment onto an image sensor.

A further operation includes determining a first lateral offset between the first linear segment and the second linear segment on the image sensor at a first time.

A further operation includes determining a second lateral offset between the first linear segment and the second linear segment on the image sensor at a second time which is subsequent to the first time.

A further operation includes determining a difference between the first lateral offset and the second lateral offset.

A further operation includes determining a distance that the eye moved relative to the first lens between the first time and the second time based on the difference between the first lateral offset and the second lateral offset.

In some embodiments, some or all of the operations may be performed by or under control of a properly-programmed processor, such as the processor 2049 of FIGS. 2A, 2B and 4.

The principles of a split-prism rangefinder system as described above may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

Figure 6A:
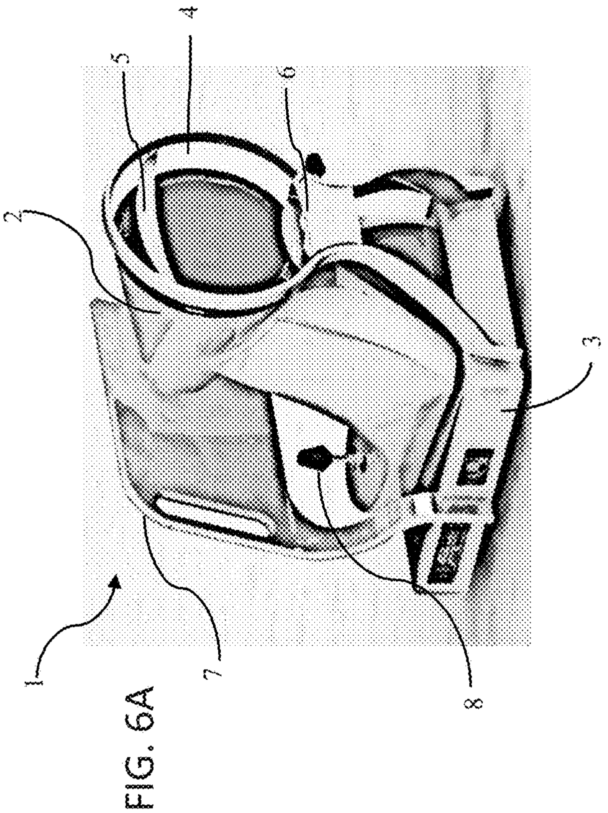
FIG. 6A illustrates a front perspective view showing an optical measurement system according to many embodiments.
Figure 6B:
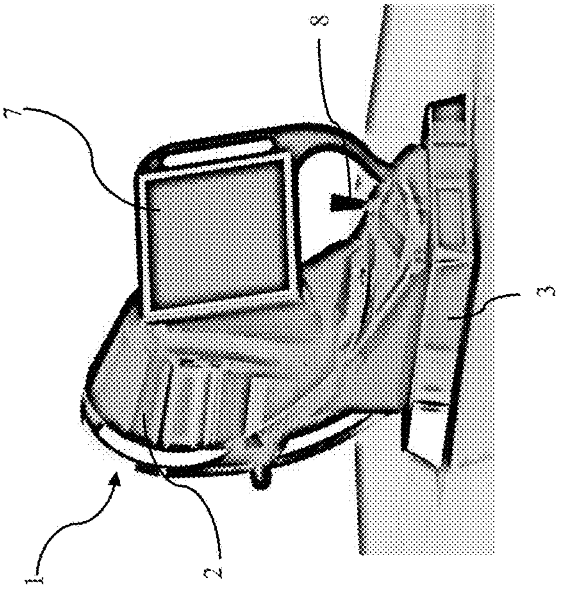
FIG. 6B illustrates a rear perspective view showing an optical measurement system according to many embodiments.
Figure 6C:
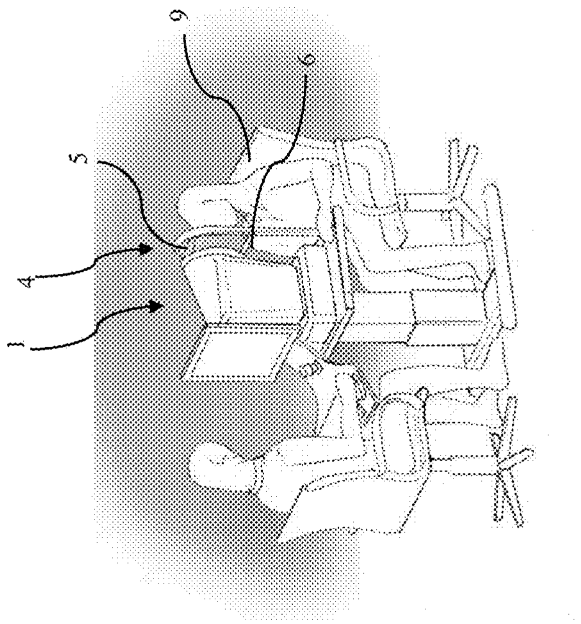
FIG. 6C illustrates a side perspective view showing an optical measurement system according to many embodiments.

As shown in FIGS. 6A-6C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of optical measurement system 1. For example, externally visible subsystems include a touch-screen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 6C, the optical measurement system I may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, optical measurement system 1 may include external communication connections. For example, optical measurement system 1 can include a network connection (e.g., an RJ45 network connection or WiFi) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival or training purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery. Other uses of network data include obtaining service logs, outcomes analysis and algorithm improvement.

Figure 7:
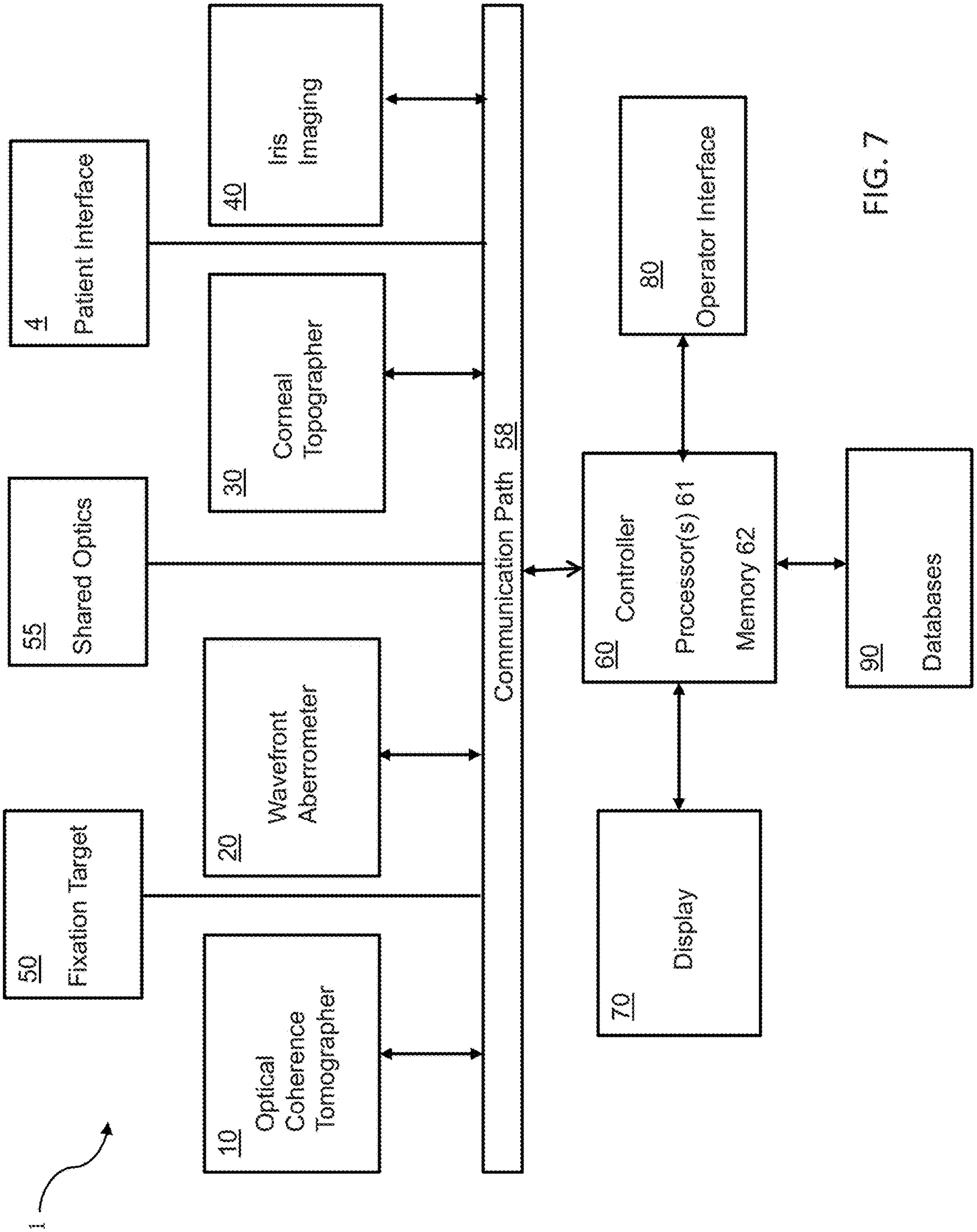
FIG. 7 is a block diagram of a system including an optical measurement instrument, and a position of an eye relative to the system according to one or more embodiments described herein which may be used by the optical measurement.

FIG. 7 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80. Optical measurement system 1 further includes patient interface 4 for a subject to present his or her eye 101 for measurement by optical measurement system 1.

As noted above, optical coherence tomography subsystem 10 may be configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for a number of purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) or spectral domain OCT (SDOCT). In some embodiments, OCT subsystem 10 may include OCT scanning subsystem 3000.

Wavefront aberrometer subsystem 20 is configured to measure ocular aberrations, which may include low and high order aberrations, by measuring the wavefront emerging from the eye by, for example a Shack-Hartman wavefront sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target subsystem 50 is configured to control the patient's accommodation and alignment direction, because it is often desired to measure the refraction and wavefront aberrations when an eye under measurement is focused at its far point Images captured by corneal topographer subsystem 10, wavefront aberrometer 20, optical coherence tomographer subsystem 30 or camera 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, camera 40, and fixation target subsystem 50. In many embodiments, shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, camera 40, fixation target subsystem 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 8A:
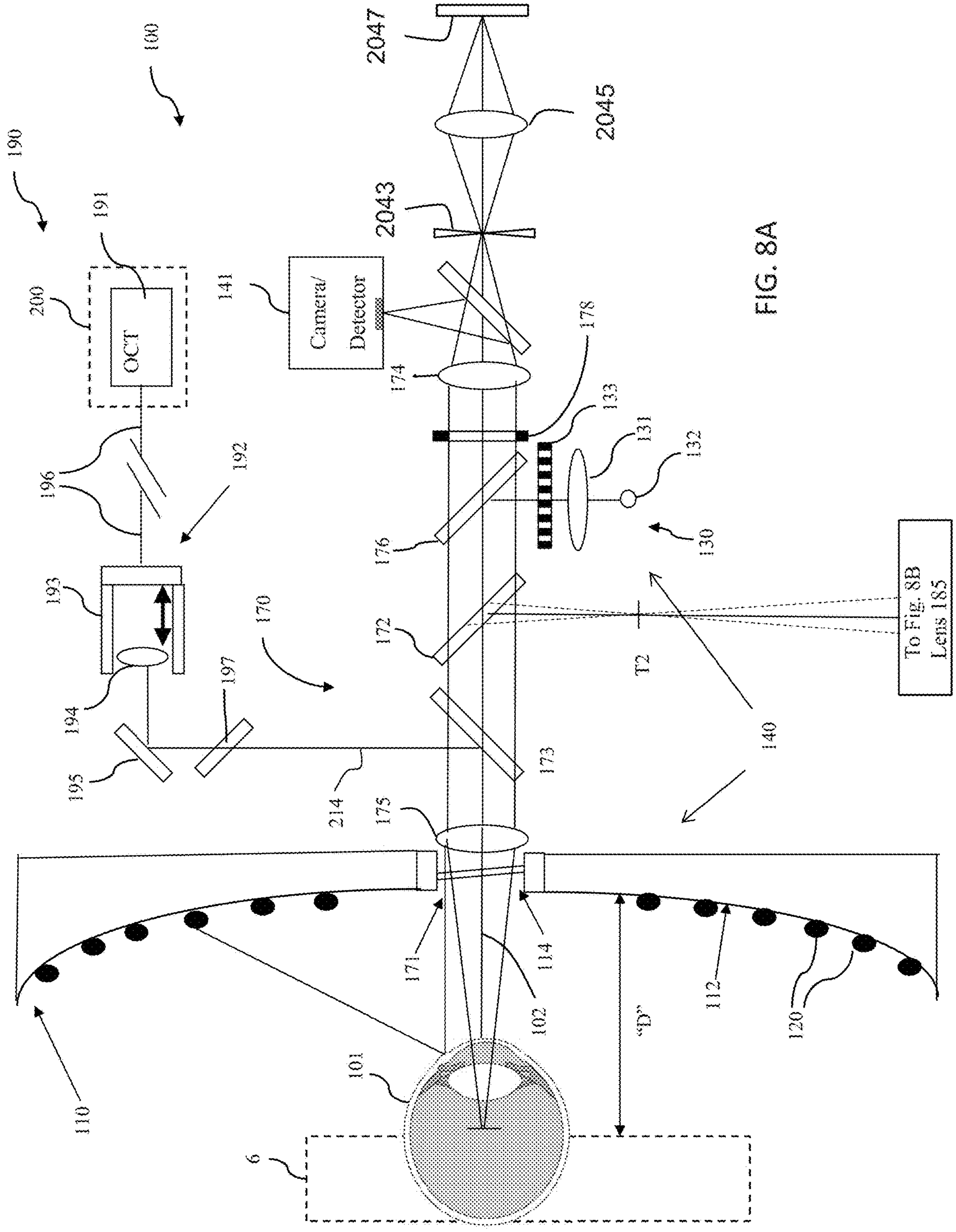
FIGS. 8A and 8B illustrate together an assembly illustrating a suitable configuration and integration of an optical coherence tomographer subsystem, a wavefront aberrometer subsystem, a corneal topographer subsystem, an iris imaging subsystem, a fixation target subsystem and a split-prism rangefinder according to a non-limiting embodiment of the present invention.
Figure 8B:
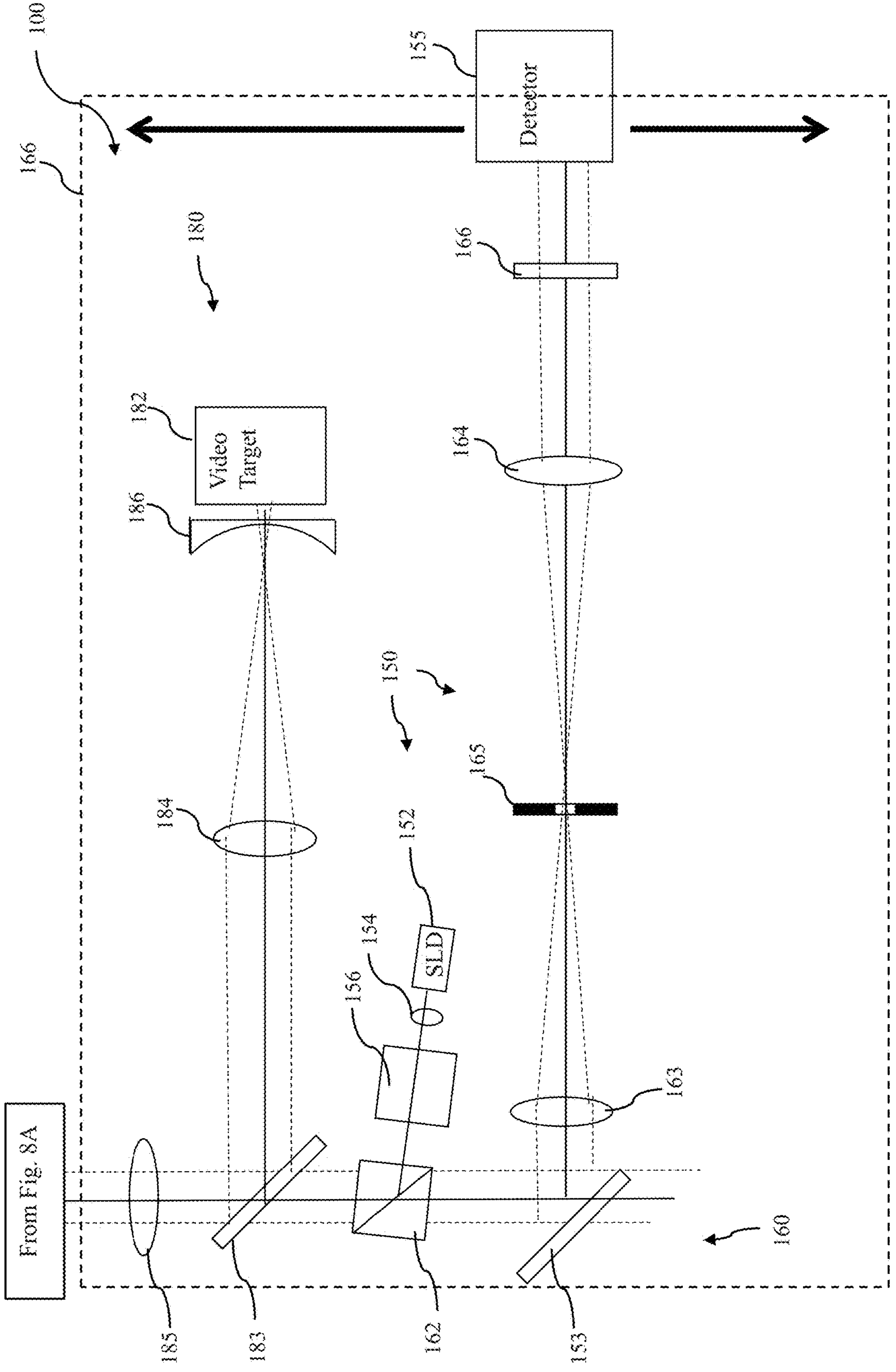

FIGS. 8A and 8B are simplified block diagrams illustrating an assembly 100 according to many embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye 101, camera 40, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 1715, an optical element (e.g., a lens) 174, a lens 1710, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141, for example a camera.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 8A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 1001 without being obstructed by the subject's nose. Of course, a variety of other configurations and shapes for principal surface 112 are possible.

In the embodiment of FIG. 8A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 8A).

In operation, a ray (solid line) from one of the first light sources 120 is reflected by the cornea and passes through optical system 170, to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 7). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the topographer portion of assembly 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by assembly 100 without a "hole" or missing data from the central corneal region.

As seen in FIG. 8A, assembly 100 also includes components of a split-prism rangefinder, including split-prism 2043, third lens 2045 and image sensor 2047. Although not shown in FIGS. 8A and 8B, assembly 100 may further include reference or range-finding light source 2010 as described above with respect to FIGS. 2A, 2B and 4.

In some embodiments, contemporaneous with obtaining the eye measurement data (e.g., wavefront aberrometry data and/or corneal topographer data) for eye 101, an image of sclera 408 of eye 101 may be captured by detector array 141. The image may be processed by a processor (e.g., processor 61 of controller 60) executing a pattern recognition algorithm as known in the art to identify unique features of sclera 408, for example scleral blood vessels. Processor 61 may execute a pattern recognition algorithm as a set of computer instructions stored in a memory (e.g., memory 62) associated with processor 61. Processor 61 may use the identified features from the image of eye 101 as fiducials or registration markers for the eye measurement data for eye 101. In some embodiments, processor 61 may store in memory 62 the eye measurement data (e.g., wavefront aberrometry data and/or corneal topographer data), a first image of eye 101 focused at the appropriate image plane for the eye measurement data (e.g., focused at iris 404 for wavefront measurement data), a second image of eye 101 focused at the fiducials (e.g., scleral blood vessels), and registration data which registers the eye measurement data to the locations of the identified features or fiducials in the image of eye 101. This set of data may be used by a surgical instrument in a subsequent surgery. For example, the surgical instrument may include a camera which is able to capture an image of eye 101, including the fiducials. By mapping the fiducials identified by assembly 100 to the same fiducials observed by the camera of the surgical instrument, the eye measurement data may be registered to the locations of the fiducials observed by the camera of the surgical instrument via the registration data of assembly 100.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor is able to better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam) under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 8A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem 190 may each comprise OCT interferometer 1000, 3000 or 4000.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse-Fourier-transformed to recover the spatial depth-dependent information for the object under test (e.g., eye 101).

In operation, as shown in FIG. 8A, after exiting connector 212, OCT probe beam 214 may be collimated, for example using a collimating optical fiber 196. Following collimating fiber 196 OCT probe beam 214 is optionally directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101. OCT probe beam 214 is then directed to beam splitter 1715 through lens 1720, and thence through lens 1710, quarter wave plate 171 and aperture 114 and to the patient eye 101. Reflections and scattering off of structures within the eye provide return beams that retrace back through the patient interface quarter wave plate 171, lens 1710, beam splitter 1715, lens 1720, Y-scan device 197, X-scan device 195, Z-scan device 193, optical fiber 196 and beam combiner 204 (FIG. 6), and back into the OCT detection device. The returning back reflections of the sample arm are combined with the returning reference portion and directed into the detector portion of the OCT detection device, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye 101 within patient interface 4.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in X, Y and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 101. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes fixation target subsystem 50 (FIG. 7), and accordingly assembly 100 shown in FIGS. 8A and 8B includes fixation target subsystem 180 which includes a fixation target 182 for the patient to view. Fixation target subsystem 180 is used to control the patient's accommodation and alignment, because it is often desired to measure the refraction and wavefront aberrations when eye 101 is focused at its far point (e.g., because LASIK treatments are primarily based on this). In fixation target subsystem 180, a projection of a target, for instance a cross-hair pattern is projected onto eye 101 of the patient, the cross hair pattern being formed, e.g. by fixation target 182 comprising a backlit LED and a film.

In operation, light originates from fixation target 182 and lenses 186 and 184. Lens 185 collects the light and forms an aerial image T2. This aerial image T2 is the one that the patient views. The patient focus is maintained on aerial image T2 during measurement so as to maintain the eye in a fixed focal position. In some embodiments, fixation target 182 may comprise a video target which may have a variable center location under control of one or more processors 61 of controller 60, for example a blinking dot which may cause aerial image T2 to appear at a plurality of different angular locations (e.g., five different angular locations) relative to eye 101. In this case, the patient may be instructed to gaze at the blinking dot as it moves from location to location to create a plurality of different gaze angles for eye 101.

Accordingly, optical coherence tomography subsystem 10 may collect OCT data sets for retina 409 for each of the plurality of gaze angles, e.g., five different gaze angles, causing five different regions of retina 409 to be sampled. In that way, in some embodiments the total combined scanned diameter retina 409 could be expanded from 3 mm to a larger region with a diameter of approximately 6 mm, providing a larger area of retina 409 from which retinal health may be evaluated.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan measures at least the locations of the retina, the cornea and one of anterior portion of the patient's lens. An iris image may be taken simultaneously with or sequentially with each of the measurements taken with wavefront aberrometry subsystem, the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the alignment of a toric IOL in the eye, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, may comprise: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, may comprise: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device may store computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position may comprise: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, may comprise: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient may comprise: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, may comprise: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a post-operative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery may comprise: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

I claim:

1. A method implemented in an instrument for making measurements of an eye, the instrument including a light source, an optical system, a split-prism rangefinder, an optical coherence tomographer (OCT) device, and a processor, the method comprising:

by the light source, producing range-finding light having a linear shape;

by the optical system, directing the range-finding light toward the eye and directing reflected range-finding light from the eye toward the split-prism rangefinder;

by the OCT device, making a first OCT measurement of the eye at a first time;

by the split-prism rangefinder, capturing a first range-finding light image of the reflected range-finding light from the eye during the first OCT measurement;

by the OCT device, changing a reference path in the OCT device;

by the OCT device, making a second OCT measurement of the eye at a second time subsequent to the first time;

by the split-prism rangefinder, capturing a second range-finding light image of the reflected range-finding light from the eye during the second OCT measurement;

by the processor, determining a movement of the eye between the first time and the second time based on the first and second range-finding light images captured by the split-prism rangefinder; and by the processor, combining the first and second OCT measurements while compensating for the movement of eye between the first time and the second time.

2. The method of claim 1, wherein the step of determining the movement of the eye between the first time and the second time includes:

determining a change in the linear shape of the returned light in the first and second range-finding light images captured by the split-prism rangefinder; and determining a distance the eye moved between the first time and the second time based on the change in the linear shape of the returned light in the first and second range-finding light images.

3. The method of claim 1, wherein the split-prism rangefinder includes a lens, a split-prism, another lens, and an image sensor, wherein the step of capturing the first range-finding light image includes:

by the lens, directing the reflected range-finding light onto the split-prism;

by the split-prism, splitting the light from the lens into first and second linear segments;

by the other lens, imaging the first and second linear segments onto an image sensor; and by the image sensor, capturing the first range-finding light image which includes the first and second linear segments; and wherein the step of capturing the second range-finding light image includes:

by the lens, directing the reflected range-finding light onto the split-prism;

by the split-prism, splitting the light from the lens into first and second linear segments;

by the other lens, imaging the first and second linear segments onto an image sensor; and by the image sensor, capturing the second range-finding light image which includes the first and second linear segments.

4. The method of claim 3, wherein the step of determining the movement of the eye between the first time and the second time includes:

determine a first lateral offset between the first and second linear segments in the first range-finding light image;

determine a second lateral offset between the first and second linear segments in the second range-finding light image; and determining the movement of the eye between the first time and the second time based on a difference between the first and second lateral offsets.

5. The method of claim 4, wherein the determining the movement of the eye is further based on a prism angle of the split-prism, an index of refraction of the split-prism, and a magnification of the other lens.

6. An instrument for making measurements of an eye, comprising:

a light source configured to produce range-finding light having a linear shape;

a split-prism rangefinder configured to receive returned range-finding light that has been reflected by the eye to determine a distance of the eye;

an optical system including at least one beamsplitter configured to direct the range-finding light from the light source toward the eye and to direct reflected range-finding light from the eye toward the split-prism rangefinder;

an optical coherence tomographer (OCT) device configured to measure structures of the eye;

a processor coupled to the split-prism rangefinder and the OCT device, wherein the processor is programed to:

control the OCT device to make a first OCT measurement of the eye at a first time;

control the split-prism rangefinder to capture a first range-finding light image of the reflected range-finding light from the eye during the first OCT measurement;

control the OCT device to change a reference path in the OCT device;

control the OCT device to make a second OCT measurement of the eye at a second time subsequent to the first time;

control the split-prism rangefinder to capture a second range-finding light image of the reflected range-finding light from the eye during the second OCT measurement;

determine a movement of the eye between the first time and the second time based on the first and second range-finding light images captured by the split-prism rangefinder; and combine the first and second OCT measurements while compensating for the movement of eye between the first time and the second time.

7. The instrument of claim 6, wherein the processor is programmed to determine the movement of the eye between the first time and the second time by:

determining a change in the linear shape of the returned light in the first and second range-finding light images captured by the split-prism rangefinder; and determining a distance the eye moved between the first time and the second time based on the change in the linear shape of the returned light in the first and second range-finding light images.

8. The instrument of claim 6, wherein the optical system includes:

a first beamsplitter configured to receive the light from the light source and to direct the light in a first direction; and a first lens located one focal length from the light source and configured to receive the light from the beamsplitter and direct the light to the eye to produce a virtual image of the linear shape in the eye, and further configured to receive returned light from the eye and provide the returned light to the beamsplitter, wherein the first beamsplitter is further configured to direct the returned light in a second direction toward the split-prism rangefinder.

9. The instrument of claim 8, wherein the split-prism rangefinder includes:

a second lens;

a split-prism;

a third lens; and an image sensor, wherein the second lens is configured to receive the returned light from the first beamsplitter and provide the returned light to the split-prism, wherein the split-prism is configured to receive the returned light from the second lens and provide the returned light to the third lens, and wherein the third lens is configured to image the returned light onto the image sensor.

10. The instrument of claim 9, wherein the split-prism is configured to split the returned light into a first linear segment and a second linear segment, wherein the first linear segment and the second linear segment are both imaged onto the image sensor.

11. The instrument of claim 10, wherein the image sensor comprises one of a complementary metal oxide semiconductor (CMOS) sensor and a line scan sensor, and includes a plurality of pixels onto which the returned light including the first linear segment and the second linear segment is imaged.

12. The instrument of claim 11, wherein the processor is configured to receive an image signal from the image sensor, wherein the image signal is generated from outputs of the pixels in response to the returned light including the first linear segment and the second linear segment.

13. The instrument of claim 12, wherein the processor is configured process the image signal to determine a first lateral offset between the first linear segment and the second linear segment at the first time, and to determine a second lateral offset between the first linear segment and the second linear segment at the second time, and to determine the distance the eye has moved relative to the first lens between the first time and the second time based on a difference between the first lateral offset and the second lateral offset.

14. The instrument of claim 13, wherein the processor is configured to determine the first lateral offset between the first linear segment and the second linear segment at the first time by determining a fractional number of pixels between a first center line of the imaged first linear segment and a second center line of the imaged second linear segment on the image sensor at the first time.

15. The instrument of claim 14, wherein the determining the movement of the eye is further based on a prism angle of the split-prism, an index of refraction of the split-prism, and a magnification of the other lens.

16. The instrument of claim 8, wherein the optical system further includes a second beamsplitter configured to direct an OCT beam generated by the OCT device toward the eye and to direct a returned portion of the OCT beam from the eye toward the OCT device.

* * * * *